(12) United States Patent
Kong et al.

(10) Patent No.: US 7,612,874 B2
(45) Date of Patent: Nov. 3, 2009

(54) METHOD AND APPARATUS FOR MONITORING OIL DETERIORATION IN REAL TIME

(75) Inventors: Hosung Kong, Seoul (KR); Eui Sung Yoon, Seoul (KR); Hung Gu Han, Seoul (KR); Lyubov Markova, Gomel (BY); Mikhail Semenyuk, Gomel (BY); Vladimir Makarenko, Gomel (BY)

(73) Assignee: Korea Institute of Science & Technology, Seoul (KR)

( * ) Notice: Subject to any disclaimer, the term of this patent is extended or adjusted under 35 U.S.C. 154(b) by 384 days.

(21) Appl. No.: 11/640,012

(22) Filed: Dec. 15, 2006

(65) Prior Publication Data

US 2008/0024761 A1    Jan. 31, 2008

(30) Foreign Application Priority Data

Jul. 27, 2006    (KR) ...................... 10-2006-0070869

(51) Int. Cl.
*G01N 33/28* (2006.01)
(52) U.S. Cl. ....................................... 356/70
(58) Field of Classification Search .................... 356/70
See application file for complete search history.

(56) References Cited

U.S. PATENT DOCUMENTS 5,194,910 A * 3/1993 Kirkpatrick et al. ........... 356/70

FOREIGN PATENT DOCUMENTS

JP    2002-124425    4/2002

\* cited by examiner

*Primary Examiner*—Gregory J Toatley, Jr.
*Assistant Examiner*—Amanda H Merlino
(74) *Attorney, Agent, or Firm*—Jones Day (57) ABSTRACT

There is provided a method and apparatus for monitoring oil deterioration in real time. The method includes the steps of radiating light into an oil medium and measuring light intensities at red, green and blue wavelength ranges of the light after passing through a certain thickness of the oil. A ratio of the light intensity at the red wavelength range to the light intensity at the green wavelength range is computed by using the measured light intensities. These steps are repeated to monitor a change in the above ratio value in real time of oil use. The apparatus includes a light source means for radiating light into an oil medium, a color sensing means for measuring light intensities at red, green and blue wavelength ranges of the light that has passed through a certain thickness of the oil, and a control means for computing and monitoring a ratio of the light intensity at the red wavelength range to the light intensity at the green wavelength range, using the light intensities measured by the color sensing means.

8 Claims, 12 Drawing Sheets

METHOD AND APPARATUS FOR MONITORING OIL DETERIORATION IN REAL TIME

The present application claims priority from Korean Patent Application No. 10-2006-0070869 filed on Jul. 27, 2006, the entire subject matter of which is incorporated herein by reference.

BACKGROUND OF THE INVENTION

1. Field of the Invention

The present invention generally relates to a method and apparatus for monitoring oil conditions in real time, and more particularly to a method and apparatus for monitoring oil by using certain parameters in order to determine an optimal timing for oil change.

2. Background of the Invention

As is commonly known, proper lubrication extends the service life of machines. When the machines are operated, a lubricant continues to be exposed to high temperatures, high speed, stress or loads, and an oxidizing environment. Thus, the lubricant tends to deteriorate and lose its lubricating effect. If the deteriorated lubricant continues to be used, then the heat becomes intensified and the lubricant is deteriorated at a faster pace. This eventually leads to significant damage or catastrophic failure of the machines.

Hydrocarbon base oils such as mineral oils and synthetic oils are chemically degraded through oxidative and thermal deterioration (thermal failure, compressive heating, etc.). Thus, chemical changes occur in the base oil molecules.

The oxidative deterioration of lubricant accelerates the depletion of antioxidant additives, thereby continuing to weaken its anti-oxidizing effect. This is worsened at the lubricating places of high temperature. In addition, this leads to the subsequent formation of corrosive acids, varnish and eventually oil-insoluble sludge. In order to prevent such occurrences, the lubricant must be properly treated or changed.

Unlike oxidation, thermal deterioration caused by heat or compressive heating is relatively not well understood. The thermal failure, which is the last step of the thermal deterioration, typically occurs when the base oil is directly exposed to hot surfaces or when there is a sudden and rapid increase of temperature associated with the adiabatic compression of entrained air bubbles in pumps and bearing, and other pressurized lubricating environments. This may cause a chemical change in the oil layer exposed to the hot surface of machine or the compressed air bubbles. Generally, the thermal failure of oils occurs at above 200° (400° F.). The thermal deterioration of oil, which causes varnish accumulation, has recently become one of the problems that occur over and over again with turbine lubricants.

Vanish may be formed from a variety of sources. In case of turbine and hydraulic oils, most varnish problems are caused through the thermal or oxidative deterioration of oil.

In order to perform an experimental evaluation of oil condition, an acid number test and a Fourier transform-infrared (FTIR) spectrometry analysis are used. In the acid number test according to ASTM D 664, a wet chemistry titration method is utilized to determine the concentration of acid present in oil. In addition, a standard FTIR analysis at laboratory is applied to the oil test. In case of the FTIR spectrometry analysis, a characteristic infrared peak at a wavenumber of 1740 $cm^{-1}$ can be used as a criterion for determining oil oxidation.

Unlike oil oxidation, the thermal deterioration of oil typically occurs when oxygen is insufficient and forms a reaction by-product containing relatively less oxygen compared to the oxidation. As such, thermal deterioration does not change the acid number. When the thermal deterioration becomes a major cause for oil deterioration, molecules containing a carbon-oxygen double bond are not formed. Thus, it does not exhibit a peak at the wavenumber of 1740 $cm^{-1}$ in the FTIR spectrum, which is used to evaluate the oxidative deterioration of base oil. However, a significant increase in the peak value in the FTIR nitration region (1600~1640 $cm^{-1}$ region of the spectrum) can indicate a thermal failure as a dominant mechanism of base oil deterioration.

However, the FTIR analysis and the total acid number (TAN) test cannot evaluate oil deterioration in a timely manner. Thus, they cannot be used for monitoring oil deterioration in real time.

U.S. Pat. No. 6,061,139 discloses a method and apparatus for monitoring thermal deterioration of a lubricant without interrupting the operation of equipment. This patent is based on the notion that the transmission loss of light, which occurs during passing through oil, is correlated with the thermal deterioration of oil. The diagnosis of lubricating oil deterioration is performed through the following steps.

a) Measuring a reference light intensity $I_o$ at a wavelength of 850 nm passing through an oil-free measuring cell having an optical length of t=1 mm.

b) Measuring a light intensity I passing through a measuring flow cell filled with test oil.

c) Computing a light transmittance loss by using equation $$L_\lambda = -\left(\frac{10}{t}\right)\log\left(\frac{I}{I_0}\right)$$

The measured light transmittance loss value of lubricant is compared with a threshold value and the result thereof is outputted in a display.

However, the above approach is disadvantageous in that the light transmittance loss is affected not only by the oil deterioration, but also by other factors such as moisture content, bubbles and particle contaminants.

One of the earliest indications for oil deterioration is a change in oil colors. Generally, the initial thermal failure causes a color change prior to the oxidative failure. Without any change in the acid number, viscosity or Fourier transform infrared oxidation (FT-IR-Ox) data of oil, a change in the oil color is a first indication for the thermal deterioration of oil. However, this means that the oxidation of oil has not yet occurred.

The change in oil color is caused mainly by carbon suspended in the oil and formation of oxidation-insoluble materials (chemical by-products caused by the failure of base oil). Oil color varies with the concentration and type of light-absorbing groups suspended in oil. These chromophore compounds are commonly referred to as color bodies.

Oil color is one of the parameters for the fresh oil specification. The color is defined according to ASTM D 1500, D1524 and D2129 standards. The ASTM has established a series of color standards ranging from colorless to dark brown. It has also assigned them numerical values ranging from 0.5 to 8.0 at intervals of 0.5. In this regard, the numerical value 8 refers to the darkest oil. These standards are made of colored glasses and oil samples can be compared side by side with the standard glasses. If a color has a value less than 0.5, then it is compared through another method using a series of platinum-cobalt standard solutions in a set of tall-form matched Nessler tubes. The platinum-cobalt scale runs from 5 to 300. These numbers denote the number of milligrams of platinum per one liter of the standard solution. The clarity of a sample is generally determined by using an oil sample, which is identical to one being used for color determination. That is, a light is focused on the sample and the signs for cloudiness, sludge or particulate matters are identified.

ASTM D 1500, D 1524 and D 2129 standards are useful in conducting laboratory oil tests. However, they are not useful for performing real-time oil monitoring. Therefore, there is a need for a new lubricant testing procedure in order to predict oil deteriorations in a timely manner.

In addition to the chemical deterioration of oil, total oil contamination indicating the physical contamination of oil is of great importance in oil performance. The oil contamination typically results from the chemical deterioration of oil and the influence of mechanical particles and water/bubble contents upon the performance of machines. The mechanical particles may originate from the system (internally or externally). The internal source includes rust, wear, sealing products, etc. The external source includes dust, welding spatter, metallic debris, etc., which can be introduced into the system through ineffective seals, unclean oil fill pipes or unclean make-up oil. Moreover, the used oil often contains water and bubbles, which originate from the outside of a system.

The total contamination of oil can be assessed by the optical density and turbidity of the oil.

U.S. Pat. No. 6,151,108 discloses a technique for measuring the contamination of lubricating oil in real time. This technique allows total contamination to be distinguished from contamination by ferrous wear particles. The total oil contamination is defined by a difference in the optical densities of fresh oil and used oil. The content of ferrous particles is measured by a change in the optical density of a test oil sample under the influence of magnetic field.

U.S. Pat. No. 6,937,332 discloses an evaluation technique of total oil contamination, which is applied to an oil quality sensor based on turbidity measurement. According to the above technique for determining oil quality, light is transmitted from a light source into a flowing liquid through a flow tube. Further, the quantity of transmitted light, which is represented by the transmitted light path, is measured by a first light sensor. The amount of perpendicular light-scattering is measured by a second light sensor, while the amount of backward light-scattering is measured by a third light sensor. The turbidity of the fluid is determined based on the measured amounts of the transmitted light, perpendicular light-scattering and backward light-scattering. It is then used for determining the quality of the fluid. The sensor can measure the total contamination of oil and the oil contamination by water and antifreeze (ethylene glycol).

The techniques disclosed in U.S. Pat. Nos. 6,151,108 and 6,937,332 may provide information on the physical state of oil. However, they cannot provide information on the chemical deterioration of oil, especially oxidative and thermal deteriorations of oil.

Therefore, the present invention seeks to resolve the above problems of the conventional technologies. In this regard, it is an object of the present invention to provide a method and apparatus for simultaneously monitoring oxidation and the thermal deterioration of oil, i.e., chemical deterioration.

Another object of the present invention is to provide a method and apparatus for monitoring oil, wherein the chemical deterioration of oil and the total contamination of oil are simultaneously computed from measured data. Further, the level of oil deterioration based on the computation is monitored in real time.

A still yet another object of the present invention is to provide an apparatus for monitoring oil deterioration in real time, which has a simplified and compact structure, thereby being mountable on every single machine to be monitored.

BRIEF DESCRIPTION OF THE DRAWINGS

Arrangements and embodiments may be described in detail with reference to the following drawings in which like reference numerals refer to like elements.

DETAILED DESCRIPTION

Hereinafter, exemplary embodiments of the present invention will now be described in detail with reference to the accompanying drawings, wherein like elements are denoted by like reference numerals.

Figure 1A:
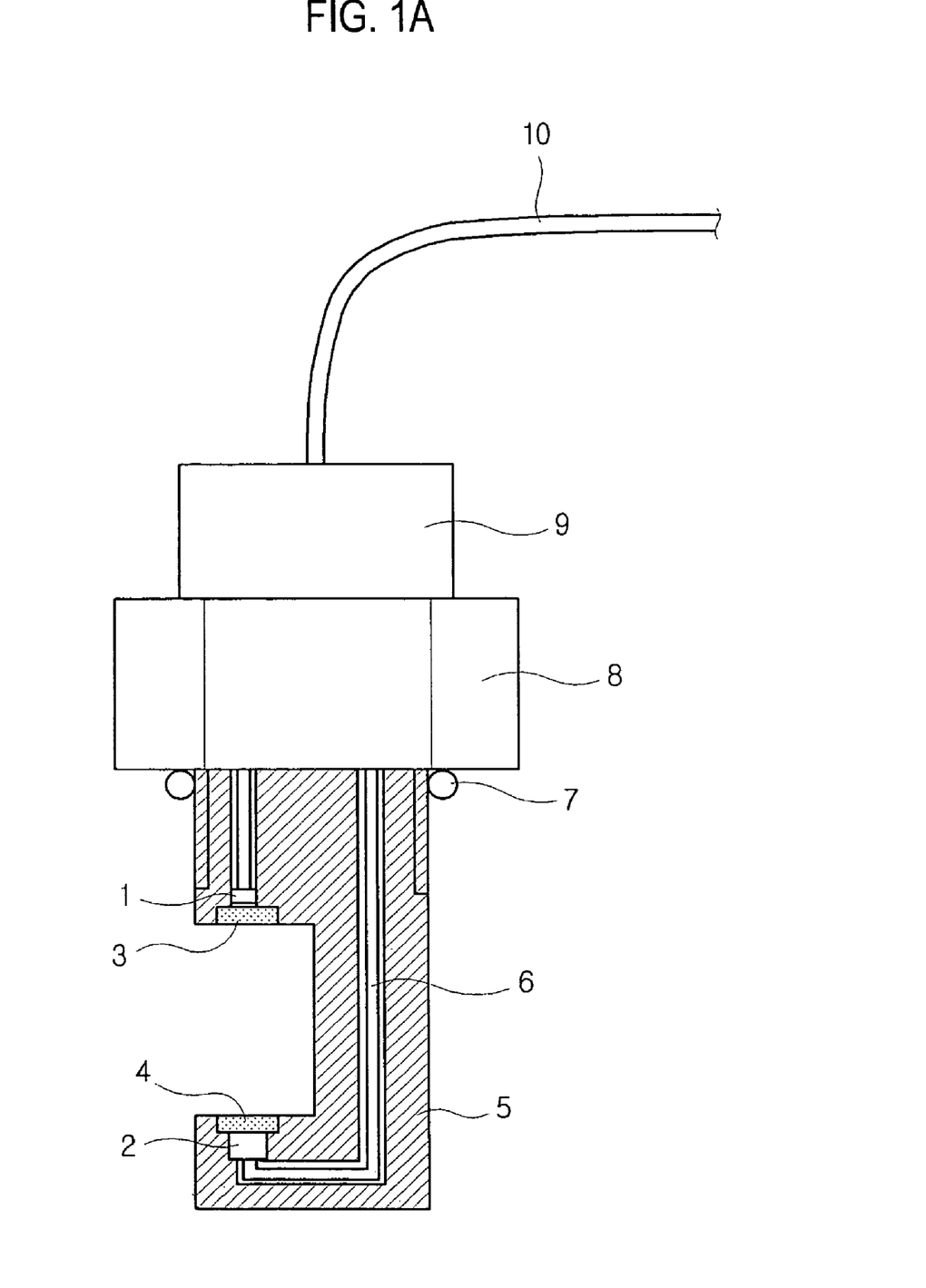
FIGS. 1A and 1B illustrate two exemplary apparatuses for monitoring oil deterioration according to an embodiment of the present invention.
Figure 1B:
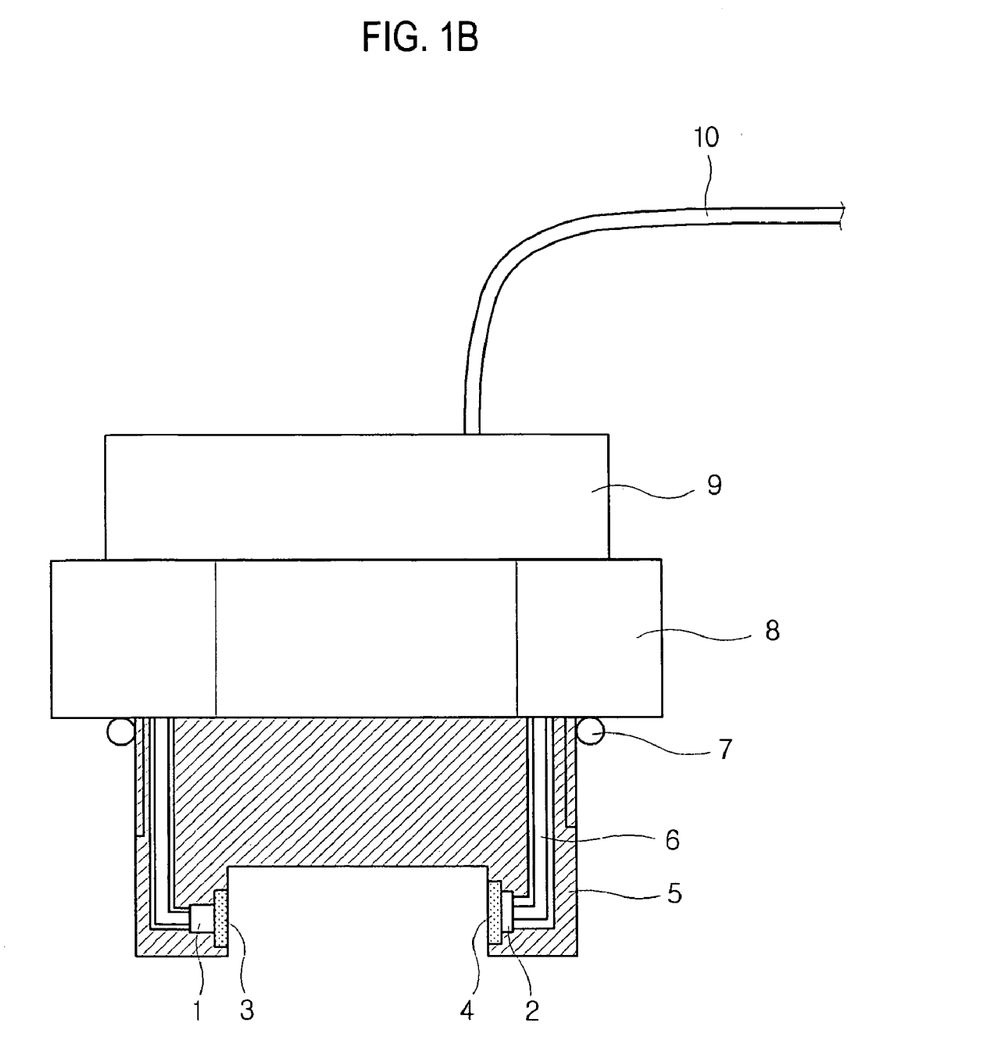
Figure 2:
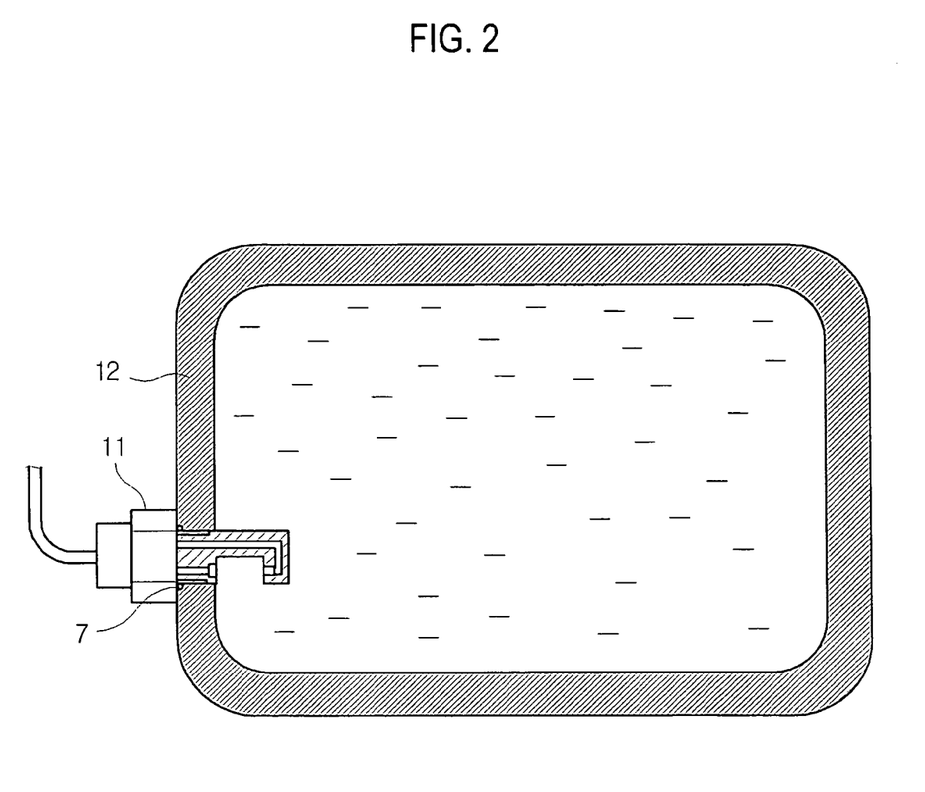
FIG. 2 illustrates a monitoring apparatus according to an embodiment of the present invention, wherein the apparatus is mounted within an oil tank.

FIGS. 1A and 1B illustrate two exemplary apparatuses for monitoring oil deterioration according to the embodiments of the present invention. FIG. 2 shows the monitoring apparatus mounted inside of an oil tank.

The apparatus of the present invention for monitoring oil deterioration in real time includes a light source unit and a color sensing unit. An oil to be monitored is placed between the light source unit and the color sensing unit. In the embodiment of FIG. 1A, the light source unit and the color sensing unit are disposed vertically against the wall of an oil container. In the embodiment of FIG. 1B, the light source unit and the color sensing unit are disposed horizontally against the wall of an oil container.

The light source unit includes a light emitter 1 and a light emitting side optical window 3. The color sensing unit includes a sensor 2 and a sensing side optical window 4. The light emitter 1 and the sensor 2 are installed in a housing 5. The housing 5 is mounted on the wall of an oil container such as oil tanks, oil circulation lines or the like. The light emitter 1 can employ an RGB LED such as B5-4RGB-CBA produced by Roithner lasertechnik, a discrete white LED produced by Marl Optosource Co., or the like. The sensor can employ a 3-element color sensor such as MCS3AT/BT produced by MAZet GmbH or TCS230 produced by Texas Advanced Optoelectronic Solutions Inc., and the like. The light emitter 1 and the sensor 2 are electrically coupled to a preamplifier circuit 9 through an electric wire 6. The preamplifier circuit 9 and a control unit are connected to each other by means of an electric cable 10. The cylindrical housing of the apparatus is provided with a thread formed at its outer circumference. The oil container is provided with a cylindrical hole for inserting the monitoring apparatus and a thread is formed at the inner surface of the cylindrical hole. The housing of the apparatus is thread-connected into the hole and fixed to the oil container such as oil circulation lines or oil tanks 12 (FIG. 2) by means of a nut 8. An O-ring is provided between the nut 8, the housing 5 and the wall of the oil container to thereby prevent oil leakage.

As shown in FIG. 2, when the apparatus 11 of the invention is installed inside of an oil tank 12, the oil is placed between the optical windows 3 and 4. Light radiated from the light emitter 2 passes through the oil and is then incident toward the sensor 2. The output current of the sensor 2 is transmitted to a control unit and display to monitor the oil condition. Although not specifically illustrated, the control unit additionally includes a signal amplifier, a processor for determining oil deterioration, and a data memory.

Figure 3:
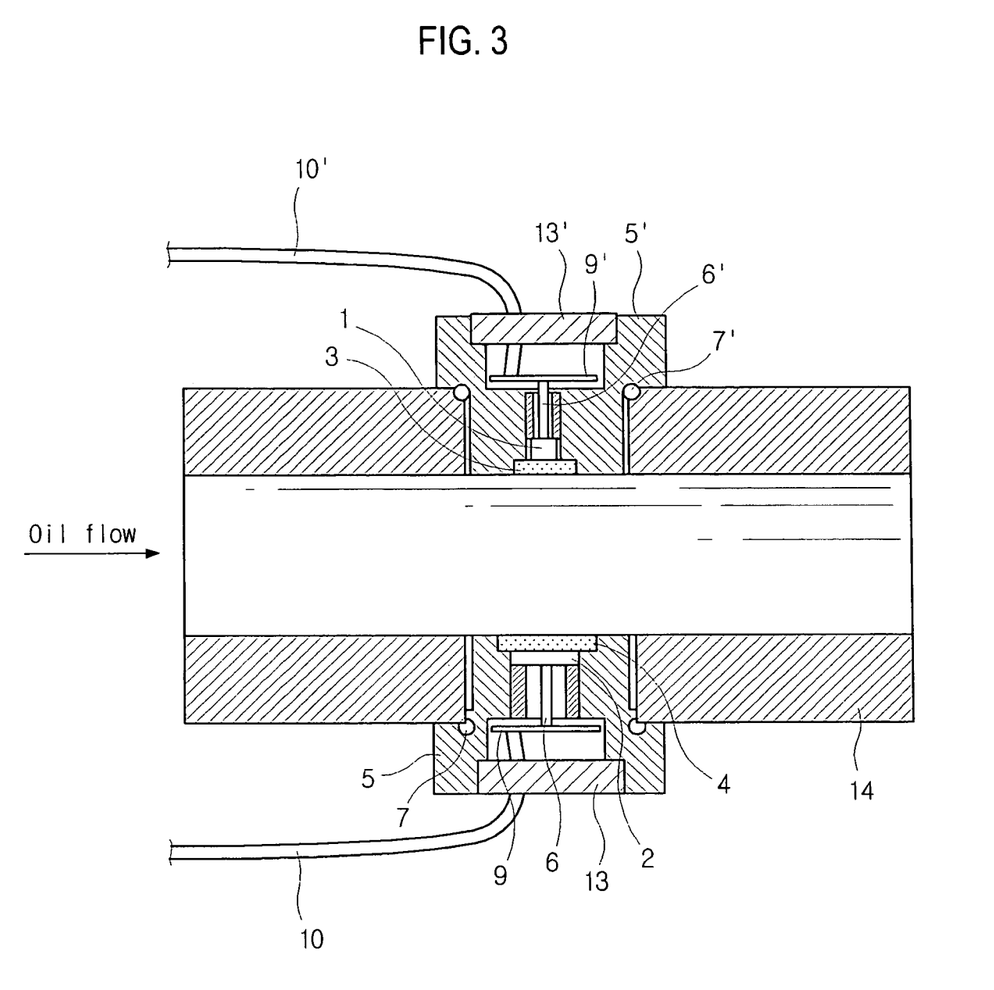
FIG. 3 illustrates a monitoring apparatus according to another embodiment of the present invention, wherein the apparatus is mounted within an oil circulation line.

FIG. 3 shows an apparatus according to another embodiment of the present invention, wherein the apparatus is mounted within an oil circulation line. In the apparatus of FIG. 3, a light source unit and a color sensing unit are installed in separate housings. The light source unit includes a light emitter 1 and a light emitting side optical window 3, and is mounted within the oil circulation line 14. The light source unit includes a first circuit 9'. The light emitter 1, the light emitting side optical window 3 and the first circuit 9' are fixed within a first housing 5', which is protected by a first cover 13'. The color sensing unit includes a sensor 2 and a sensing side optical window 4, and is mounted within the oil circulation line 14 so as to face the light source unit. The color sensing unit may further include a second circuit 9. The sensor 2, the sensing side optical window 4 and the second circuit 9 are fixed inside a second housing 5, which is protected by a second cover 13. The light emitter 1 and the first circuit 9' are interconnected through a first electric wire 6'. The sensor 2 and the second circuit 9 are interconnected through a second electric wire 6. The first and second circuits 9' and 9 are coupled to a control unit (not shown).

According to the present invention, light radiated from the light emitter 1 passes through the oil and then becomes incident on the sensor 2, which measures the light intensity in three wavelength ranges of red, green and blue.

Figure 4:
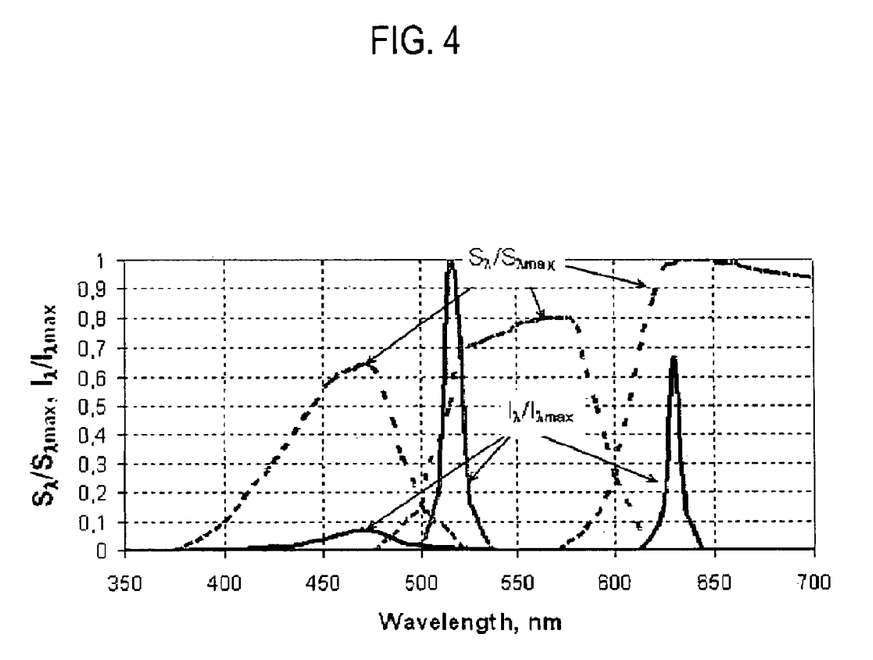
FIG. 4 is a graph showing a relative spectral luminous intensity for an RGB LED and a relative spectral sensitivity for a color sensor MCS3AT/BT (produced by MAZet GmbH) according to an embodiment of the present invention.
Figure 5:
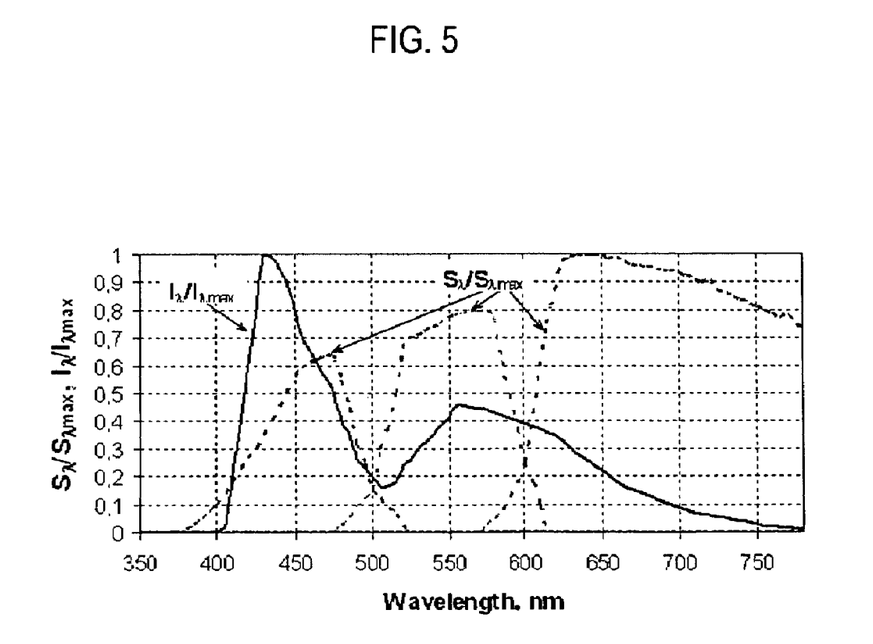
FIG. 5 is a graph showing a relative spectral luminous intensity for a white LED and a relative spectral sensitivity for a color sensor MCS3AT/BT (produced by MAZet GmbH) according to another embodiment of the present invention.
Figure 6A:
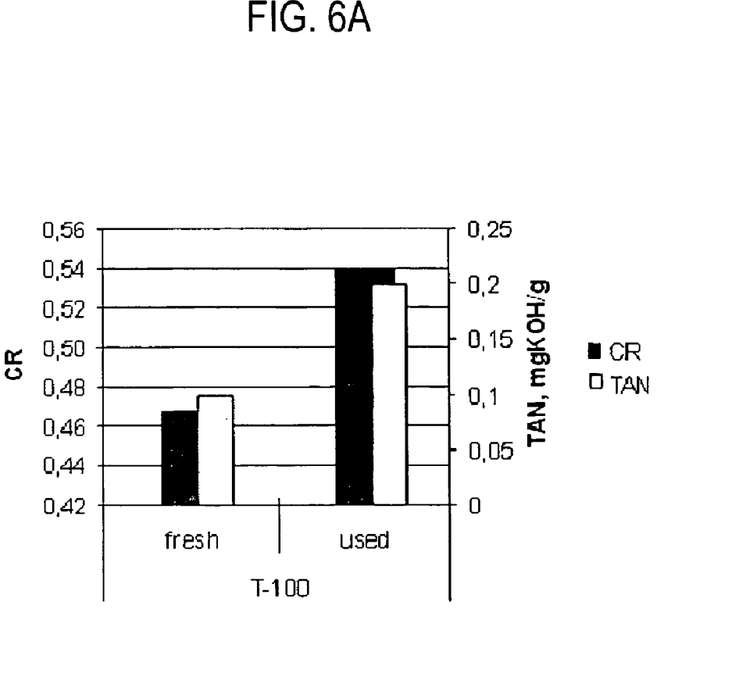
FIGS. 6A to 6D are graphs showing a correlation between a chromatic ratio (CR) and a total acid number (TAN) parameter with respect to a mineral oil (Teresstic T-100, Rando HD-32, DTE-24) and a synthetic oil (Cosmolubric HF-130) as fresh and used oils when the light emitting means employs a white LED.
Figure 6B:
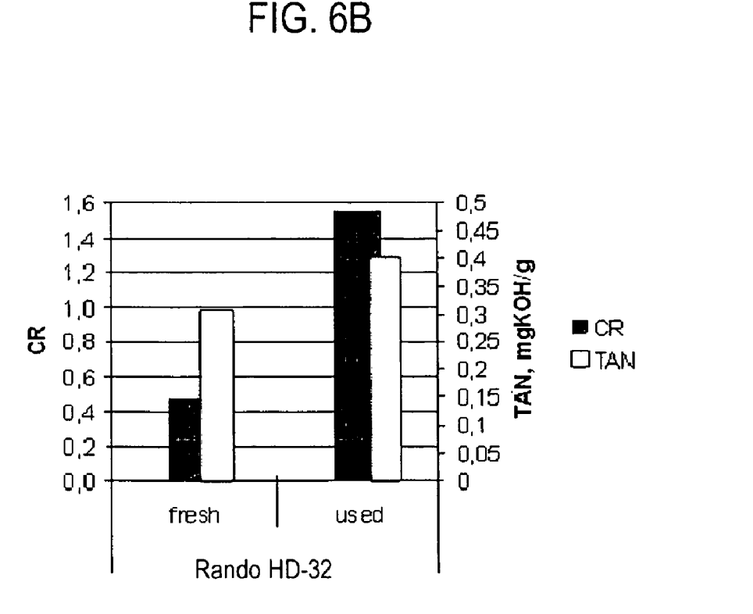
Figure 6C:
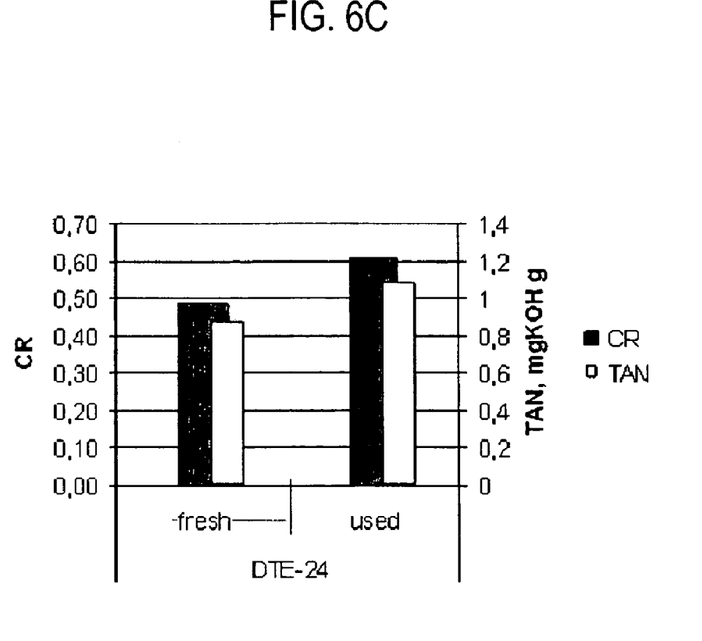
Figure 6D:
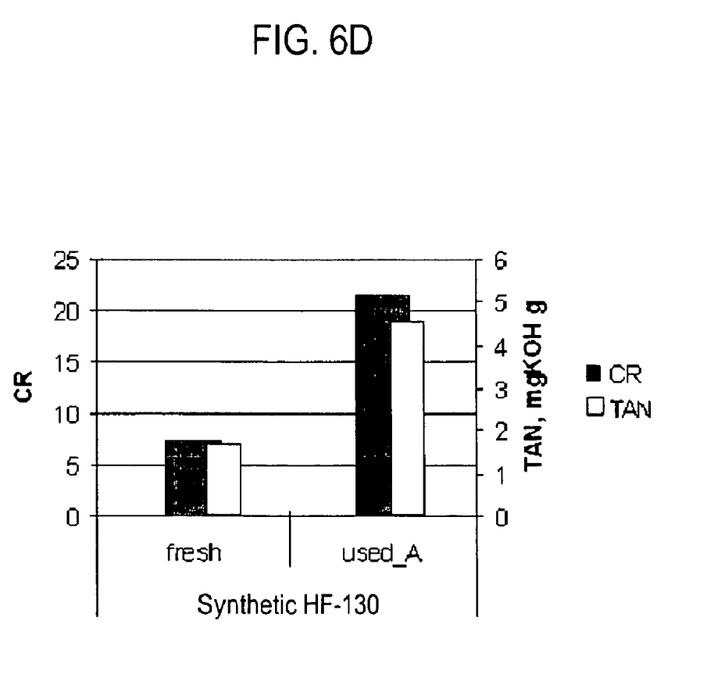

FIG. 4 is a graph showing a relative spectral luminous intensity $I_\lambda/I_{\lambda,max}$ of an RGB LED and a relative spectral sensitivity $S_\lambda/S_{\lambda,max}$ of a color sensor MCS3AT/BT (produced by MAZet GmbH). FIG. 5 is a graph showing a relative spectral luminous intensity $I_\lambda/I_{\lambda,max}$ of a white LED and a relative spectral sensitivity $S_\lambda/S_{\lambda,max}$ for a color sensor MCS3AT/BT (produced by MAZet GmbH).

The above light emitter and sensor are used to evaluate the oil color change to determine the chemical deterioration of oil, as well as to perform the measurement of a change in oil optical densities at three optical wavelength ranges in order to evaluate total oil contamination.

The evaluation of a change in oil colors employs a chromatic ratio (CR), which is used as a parameter for the chemical quality of oil. The chromatic ratio is defined by a ratio of the light intensity transmitted through oil at the red wavelength range to that transmitted through oil at the green wavelength range. According to Saurabh Kumar, et al., "Additives Depletion and Engine Oil Condition—A Case Study," Industrial Lubrication and Tribology, Vol. 57, No. 2, 2005, pp. 69-72, and Jarmo Vanhanen, et al., "Characterization of Used Mineral Oil Condition by Spectroscopic Techniques," Applied Optics, Vol. 43, No. 24, 2004, pp. 4719-4722, light is strongly absorbed at the blue wavelength range. Thus, in order to evaluate a change in oil color towards a longer wavelength, the chromatic ratio is determined by using a red color sensor output $U_R$ and a green color sensor output $U_G$, as follows.

$$CR = \frac{U_R}{U_G}$$

As the oil service time becomes longer, the chromatic ratio becomes higher. That is, the contribution to the oil color becomes lower at the green wavelength range and higher at the red wavelength range.

Figure 7:
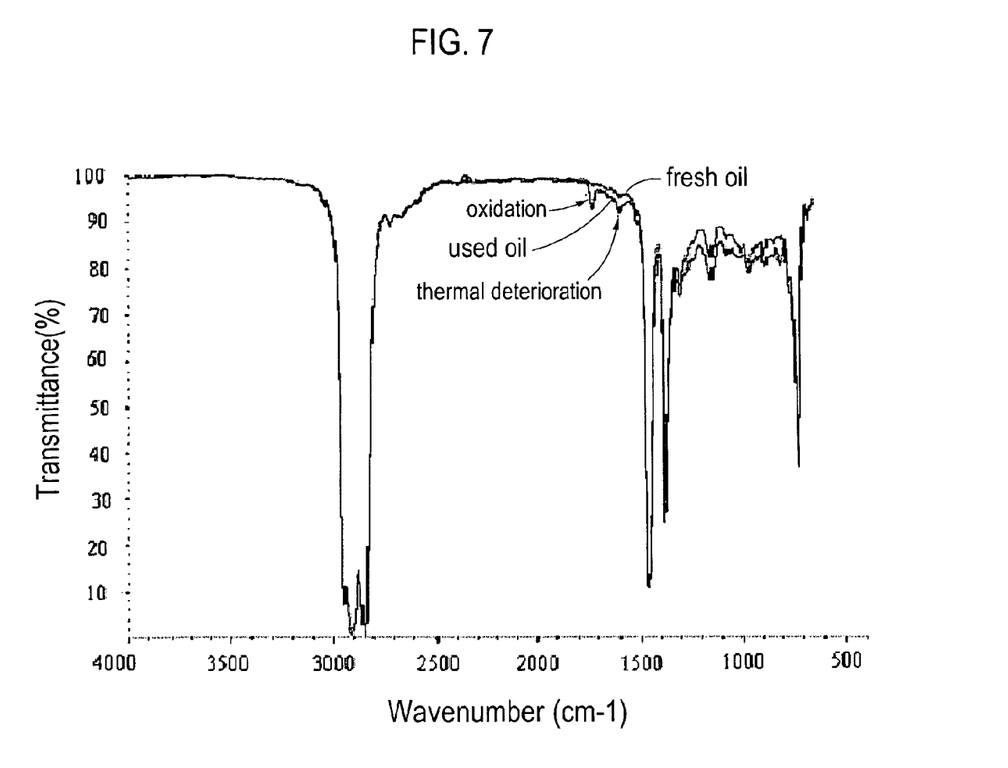
FIG. 7 is a graph showing a FTIR transmittance spectrum for hydraulic oil (Rando HD-32) as fresh and used oils.

FIGS. 6A to 6D are graphs showing a correlation between a chromatic ratio (CR) and a total acid number (TAN) parameter with respect to a mineral oil (Teresstic T-100, Rando HD-32, DTE-24) and a synthetic oil (Cosmolubric HF-130) as fresh and used oils when the light emitting means employs a white LED. Referring to FIGS. 6a to 6d, among the tested oils, it can be seen that Teresstic T-100, DTE-24 and HF-130 exhibit a strong correlation between CR and TAN, as a change in parameters of CR and TAN in the fresh and used oils. However, in case of Rando HD-32 oil test, the CR parameter shows a significant difference in the fresh and used oils, but the TAN parameter exhibits a smaller difference in the fresh and used oils. According to the result of FTIR analysis, as shown in FIG. 7, the Rando HD-32 used oil shows a peak value at the wavenumber of 1610 cm$^{-1}$ of the transmittance spectrum. This means that the used oil is thermally deteriorated. That is, it has been discovered from the above results that TAN can be used only for evaluating oil oxidation and CR parameter correctly reflects the chemical deterioration of oil in terms of both oil oxidation and thermal deterioration.

In addition, the method of the present invention provides an assessment of total oil contamination. The total oil contamination is caused by not only the content of water, but also by the content of dust contaminants, wear debris and oxidation and aging products. This oil contamination can be evaluated using a change in the optical density of fresh and used oils.

The change in the optical density of oil is evaluated separately in three wavelength ranges (red $\Delta D_R$, green $\Delta D_G$, and blue $\Delta D_B$) by using the following equations.

$$\Delta D_R = D_{R,used} - D_{R,fresh} = \ln \frac{U_{R,fresh}}{U_{R,used}} \quad \text{[Equation 1]}$$

$$\Delta D_G = D_{G,used} - D_{G,fresh} = \ln \frac{U_{G,fresh}}{U_{G,used}} \quad \text{[Equation 2]}$$

$$\Delta D_B = D_{B,used} - D_{B,fresh} = \ln \frac{U_{B,fresh}}{U_{B,used}} \quad \text{[Equation 3]}$$

In the above equations 1 to 3, $D_{R,fresh}$, $D_{G,fresh}$ and $D_{B,fresh}$ denote the optical densities of fresh oil at the red, green and blue wavelength ranges, respectively. $D_{R,used}$, $D_{G,used}$ and $D_{B,\,used}$ denote the optical densities of the used oil at the red, green e wavelength ranges, respectively. $U_{R,fresh}$, $U_{G,fresh}$ and $U_{B,fresh}$ denote the outupt signals at the red, green and blue wavelength ranges, respectively, in the fresh oil test. $U_{R,\,used}$, $U_{G,\,used}$ and $U_{B,\,used}$ denote the output signals at the red, green and blue wavelength ranges, respectively, in the used oil test.

Figure 8A:
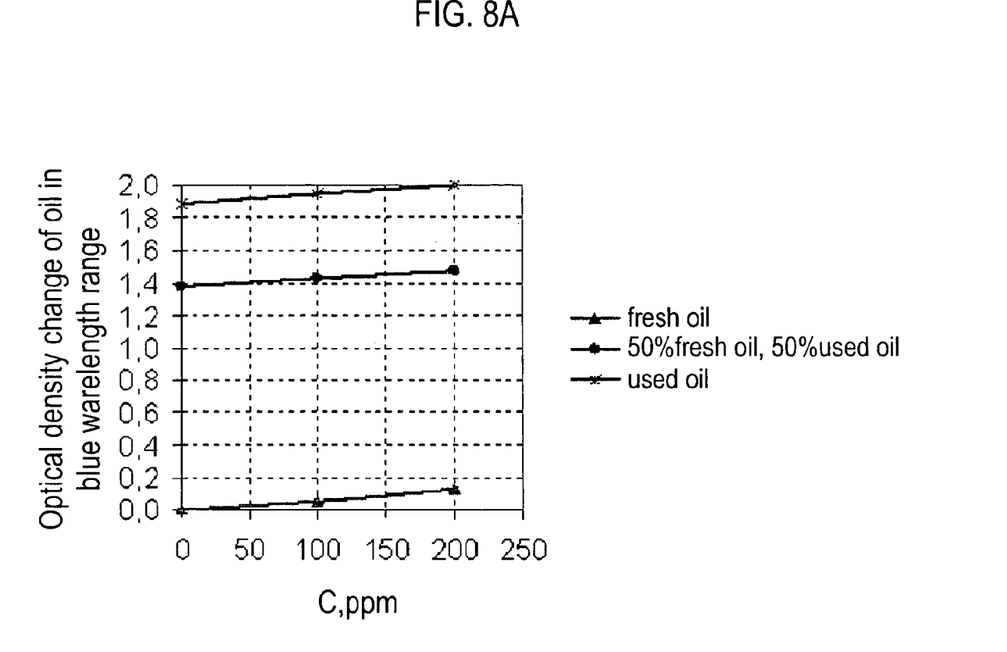
FIGS. 8A to 8C are graphs representing an oil optical density in red, green and blue wavelength ranges as a function of dust contents with respect to fresh oil, used oil, and a mixture of 50% fresh oil and 50% used oil.
Figure 8B:
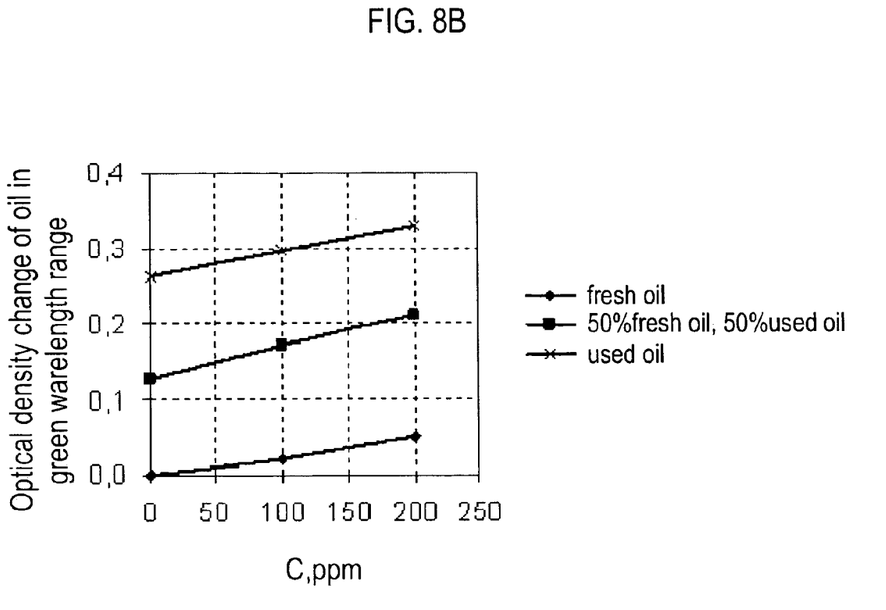
Figure 8C:
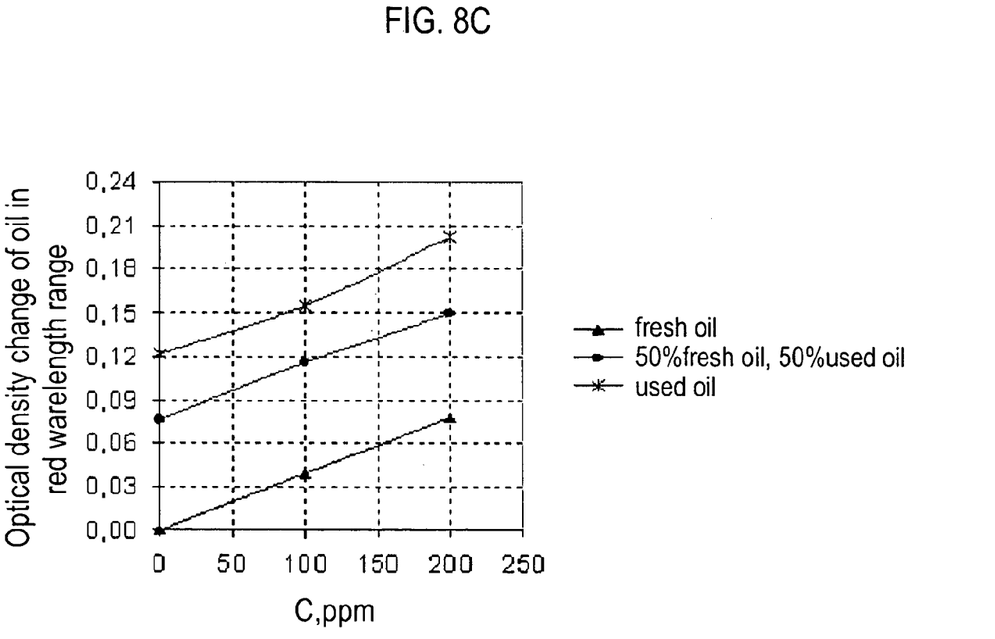

FIGS. 8A to 8C are graphs representing an oil optical density in red, green and blue wavelength ranges as a function of dust contents with respect to fresh oil, used oil, and a mixture of 50% fresh oil and 50% used oil.

Arizona Test Dust (ISO 12103-1, A3 Medium Test Dust with nominal 0-80 micron size) was used in the test. Referring to FIGS. 8A to 8C, it can be seen that as the dust content increases, the change in the optical density at the red, green and blue wavelength ranges increases.

Figure 9:
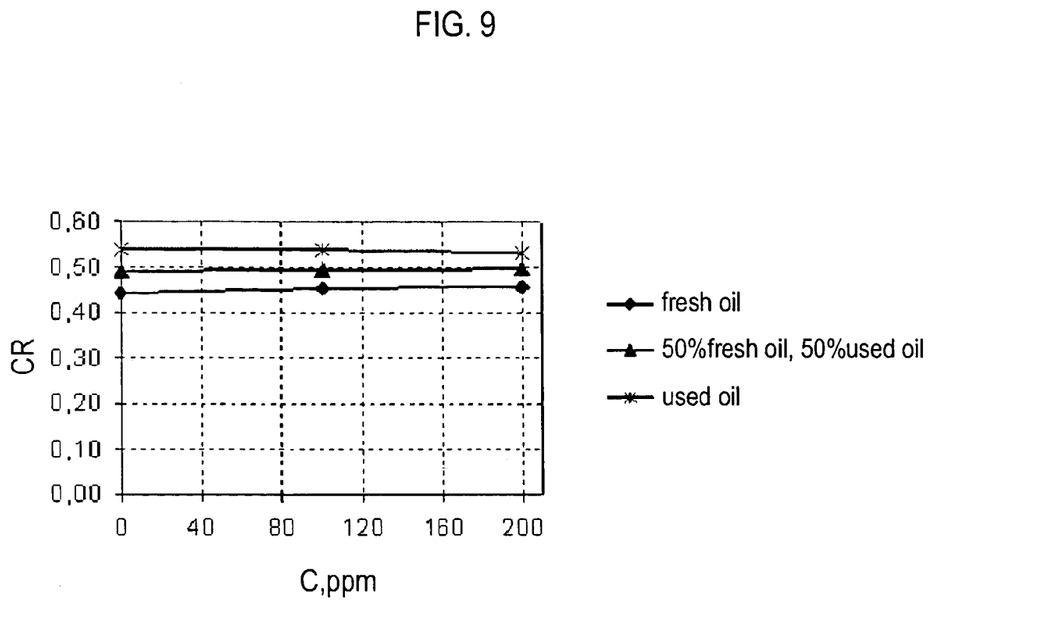
FIG. 9 is a graph showing a chromatic ratio (CR) parameter as a function of dust particle concentrations.

FIG. 9 is a graph showing a chromatic ratio (CR) parameter as a function of dust particle concentrations. As shown in FIG. 9, it should be noted that CR value is independent on the mechanical contamination of oil. Therefore, in the method according to the present invention, the chromatic ratio CR and the changes in the optical densities ($\Delta D_R$, $\Delta D_G$ and $\Delta D_B$) are used to evaluate the chemical oil deterioration and total oil contamination.

The measured values for the chromatic ratio CR and the changes in the optical densities ($\Delta D_R$, $\Delta D_G$ and $\Delta D_B$) are compared with predetermined threshold values.

If the measured CR value is below the threshold value, then the oil is evaluated to have a good chemical condition. If the CR value is above the threshold, then the oil is in an unacceptable chemical condition.

If the measured changes in the optical densities at the blue, red and green wavelength ranges are below the threshold values, then the oil has a satisfactory level of total contamination. If the measured changes in the optical densities at the blue, red and green wavelength ranges are above the threshold values, then the oil has an unacceptable level of total contamination.

If the measured CR and changes in the optical densities at the blue, green and red wavelength ranges are below the threshold values, then the oil is in a good condition. If the measured CR and changes in the optical densities at the blue, green and red wavelength ranges are above the threshold values, then the oil is determined to be in an unacceptable condition.

This information on the oil condition can be outputted through a display.

As described above, the chromatic ratio parameter of the present invention can be used for precisely and simultaneously monitoring chemical deterioration corresponding to the oxidation and thermal deterioration of oil. In addition, the present invention provides a method and apparatus for monitoring the deterioration level of oil in real time based on the level of chemical deterioration and the total contamination of oil.

In addition, according to the present invention, the deterioration level of oil is compared with a threshold value, thereby informing the user of an optimal time for oil change in a timely manner. As such, it can prevent the subject machine from being damaged or broken due to oil deterioration.

Furthermore, the apparatus of the present invention has a simplified structure and can be manufactured in a compact form, thereby being capable of being equipped in every single machine to be monitored while being manufactured in a cost-efficient manner.

The present invention may be achieved in whole or in part by a method of monitoring oil deterioration in real time, wherein said method comprises the steps of: radiating light into an oil medium; measuring light intensities at red, green and blue wavelength ranges of the light after passing through a certain thickness of the oil; computing a ratio of the light intensity at the red wavelength range to the light intensity at the green wavelength range; and using the measured light intensities, wherein the steps are repeated to monitor a change in the ratio of the light intensity at the red wavelength range to the light intensity at the green wavelength range in real time of oil use.

Preferably, the method of the present invention may further comprise the step of comparing the ratio of the light intensity at the red wavelength range to the light intensity at the green wavelength range with a predetermined threshold value.

According to another aspect of the present invention, different embodiments may be achieved in whole or in part by a method of monitoring oil deterioration in real time, wherein said method comprises the steps of: radiating light into an oil medium; measuring light intensities at red, green and blue wavelength ranges of the light after passing through a certain thickness of the oil; and computing a ratio of the light intensity at the red wavelength range to the light intensity at the green wavelength range using the measured light intensities, and a change in oil optical density in the red, green and blue wavelength ranges between initial and current conditions of the oil, wherein the steps are repeated in real time of oil use to monitor a change in the ratio of the light intensity at the red wavelength range to the light intensity at the green wavelength range and the change in the oil optical density.

Preferably, the method of the present invention may further comprise the step of comparing the ratio of the light intensity at the red wavelength range to the light intensity at the green wavelength range with a predetermined threshold value of the ratio and comparing the changes in the oil optical density in the red, green and blue wavelength ranges with a predetermined threshold values of the changes.

According to a further aspect of the present invention, other embodiments may be achieved in whole or in part by an apparatus for monitoring oil deterioration in real time, wherein said apparatus comprises: a light source means for radiating light into an oil medium; a color sensing means for measuring light intensities at red, green and blue wavelength ranges of the light, which has passed through a certain thickness of the oil; and a control means for computing and monitoring a ratio of the light intensity at the red wavelength range to the light intensity at the green wavelength range, the control means being configured to use the light intensities measured by the color sensing means.

Preferably, the control means further computes a change in oil optical density in the red, green and blue wavelength ranges between initial and current conditions of the oil by using the light intensities measured by the color sensing means and simultaneously monitoring the ratio and the change.

In addition, the apparatus may further comprise a display coupled to the control means, wherein the display outputs a level of oil deterioration comparing the values computed by the control means with a predetermined threshold value.

The light source means may include a light emitter and a light emitter side optical window disposed between the light emitter and the oil. Further, the color sensing means may include a sensor and a light sensing side optical window disposed between the sensor and the oil.

The light emitter includes an RGB LED or a white LED. Further, the sensor may be a color sensor.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

While the present invention has been described and illustrated with respect to a preferred embodiment of the invention, it will be apparent to those skilled in the art that variations and modifications are possible without deviating from the broad principles and teachings of the present invention, which should be limited solely by the scope of the claims appended hereto.

What is claimed is:

1. A method of monitoring oil deterioration in real time, comprising the steps of:
    radiating light into an oil medium;
    measuring light intensities at red, green and blue wavelength ranges of the light after passing through a certain thickness of the oil; and
    computing from the measured light intensities a ratio of the light intensity at the red wavelength range to the light intensity at the green wavelength range, and a change in oil optical density between initial and current conditions of the oil;
    wherein the steps are repeated over a period of oil use to monitor a change in the ratio of the light intensity at the red wavelength range to the light intensity at the green wavelength range and the change in the oil optical density in the red, green and blue wavelength ranges.

2. The method of claim 1, further comprising comparing the ratio of the light intensity at the red wavelength range to the light intensity at the green wavelength range with a predetermined threshold value of the ratio and comparing the change in the oil optical density in the red, green and blue wavelength ranges with a predetermined thresholds value of the change.

3. An apparatus for monitoring oil deterioration in real time, the apparatus comprising:
    a light source means for radiating light into an oil medium;
    a color sensing means for measuring intensities at red, green and blue wavelength ranges of the light that has passed through a certain thickness of the oil; and
    a control means for computing and monitoring a ratio of the light intensity at the red wavelength range to the light intensity at the green wavelength range, the control means being configured to use the light intensities measured by the color sensing means,
    wherein the control means further computes a change in oil optical density between initial and current conditions of the oil by using the light intensities measured by the color sensing means and simultaneously monitoring the ratio and the change.

4. The apparatus of claim 3, further comprising a display coupled to the control means, wherein a level of oil deterioration is outputted through the display by comparing the values computed by the control means with a predetermined threshold value.

5. The apparatus of claim 3, wherein the light source means includes a light emitter and a light emitter side optical window disposed between the light emitter and the oil, and wherein the color sensing means includes a sensor and a light sensing side optical window disposed between the sensor and the oil.

6. The apparatus of claim 5, wherein the light emitter includes an RGB LED.

7. The apparatus of claim 5, wherein the light emitter includes a white LED.

8. The apparatus of claim 5, wherein the sensor is a color sensor.

* * * * *